US005637488A

United States Patent [19]
Medabalimi et al.

[11] Patent Number: 5,637,488
[45] Date of Patent: *Jun. 10, 1997

[54] HIV PROTEASE GENE AND METHOD FOR ITS EXPRESSION

[75] Inventors: John L. Medabalimi, Silver Spring; Stephen Oroszlan, Potomac; Peter T. Mora, Chevy Chase, all of Md.

[73] Assignee: The United States of America as represented by the Department of Health and Human Services, Washington, D.C.

[*] Notice: The term of this patent shall not extend beyond the expiration date of Pat. No. 5,252,477.

[21] Appl. No.: 24,916

[22] Filed: Mar. 2, 1993

Related U.S. Application Data

[63] Continuation of Ser. No. 662,508, Feb. 28, 1991, abandoned, which is a continuation of Ser. No. 218,304, Jul. 13, 1988, abandoned, which is a continuation-in-part of Ser. No. 57,183, Jun. 1, 1987, Pat. No. 5,252,477.

[51] Int. Cl.$^6$ .......................... C12N 15/49; C12N 15/63; C12N 15/70; C12P 21/02
[52] U.S. Cl. .................. 435/172.3; 435/219; 435/320.1; 536/23.72; 930/221; 935/33; 935/34; 935/38
[58] Field of Search ................................ 435/69.3, 69.1, 435/172.3, 219; 536/23.1, 23.2

[56] References Cited

U.S. PATENT DOCUMENTS 5,001,230  3/1991  Brown et al. .......................... 536/23.5
5,252,477  10/1993  Oroszlan et al. ....................... 435/219

FOREIGN PATENT DOCUMENTS 3800233  7/1989  Germany.

OTHER PUBLICATIONS

J. Hansen et al., "Partial Purification and Substrate Analysis of Bacterially Expressed HIV Protease by Means of Monoclonal Antibody"; Embo Journal, vol. 7 No. 6, Jun. 1988, pp. 1785–1791.

N. E. Kohl et al., "Active Human Immunodeficiency Virus Protease is Required for Viral Infectivity"; Proceedings of the National Academy of Sciences of USA, vol. 85, No. 13, Jul. 1988, pp. 4686–4690.

M.C. Graves et al., "An 11–kDa Form of Human Immunodeficiency Virus Protease Expressed in *Escherichia coli* is Sufficient for Enzymatic Activity"; Proc. Natl. Acad. Sci. USA, vol. 85, Apr. 1988, pp. 2449–2453.

J. Mous et al., "Processing Protease and Reverse Transcriptase From Human Immunodeficiency Virus Type I Polyprotein in *Escherichia coli*"; Journal of Virology, vol. 62, No. 4, Apr. 1988, pp. 1433–1436.

N. T. Chang et al (1985) Science 228:93–96.

T. Yasunaga et al. (1986) FEBS Letters 199(2):145–150.

S. H. Nam et al. (1993) J. Virology 67(1):196–203.

Ratner, et al. *Nature* 313:277–284, 1985.

Wain – Hobson, et al. *Cell* 40:9–17, 1985.

Farmerie, W. *Science* 236:305–308, 1987.

Debouk, et al. PNAS USA 84:8903–8906, 1987.

*Primary Examiner*—Jacqueline M. Stone
*Assistant Examiner*—Johnny F. Railey, II
*Attorney, Agent, or Firm*—Morgan & Finnegan

[57] ABSTRACT

The invention is a synthetic DNA sequence for encoding a specific enzyme or protease. The protease is essential for the completion (replication) of an infective human immunodeficiency virus (HIV). The invented gene is desirable for the expression of the protease by recombinant methodology in prokaryotic and/or eukaryotic cells and the production of a commercially desirable amount of the protease for biochemical and physical characterization, necessary to find effective inhibitor of the protease, and thereby to block the production of infectious human immunodeficiency virus (HIVs).

9 Claims, 4 Drawing Sheets

```
fragment 1
5'  CCTCAGATCACTCTTTTGGCAACGACCCCTCGTCACAATAAAGATAGGGGGCAActaa fragment 2
       AGGAAGCTCTATTAGATACAGGAGCAGATGATACAGTATTAGAAGAAATGAGTTTGCCAGGAagat fragment 3
          GGAAACCAAAAATGATAGGGGGAATTGGAGGTTTTATCAAAGTAAGACAGTATGATCAgata fragment 4
            CTCATAGAAATCTGTGGACATAAAGCTATAGGTACAGTATTAGTAGGACCTACACCTGTcaac fragment 5
               ATAATTGGAAGAAATCTGTTGACTCAGATTGGTTGCACTTTAAATTTT    3'
```

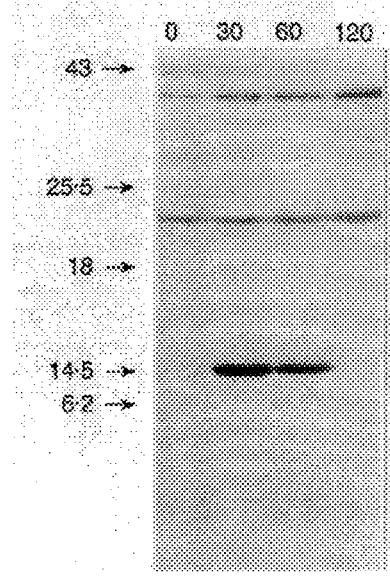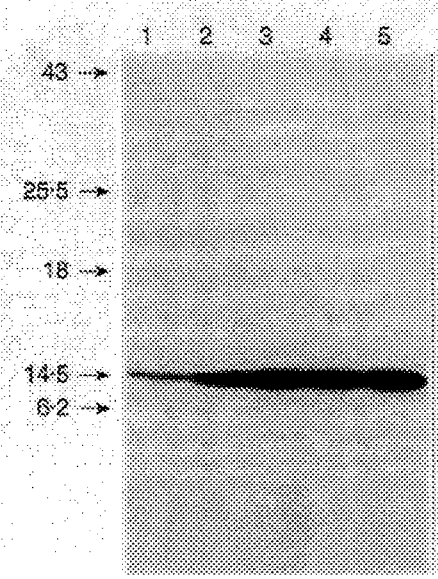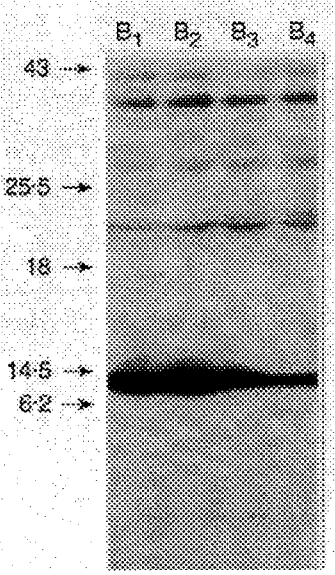

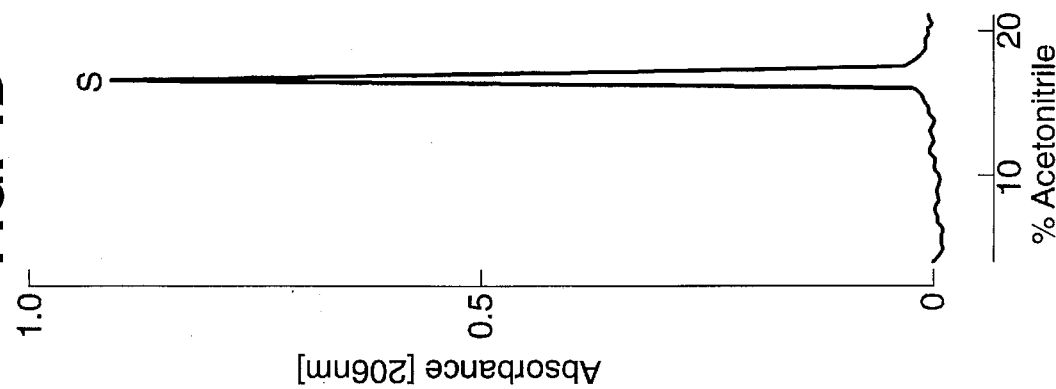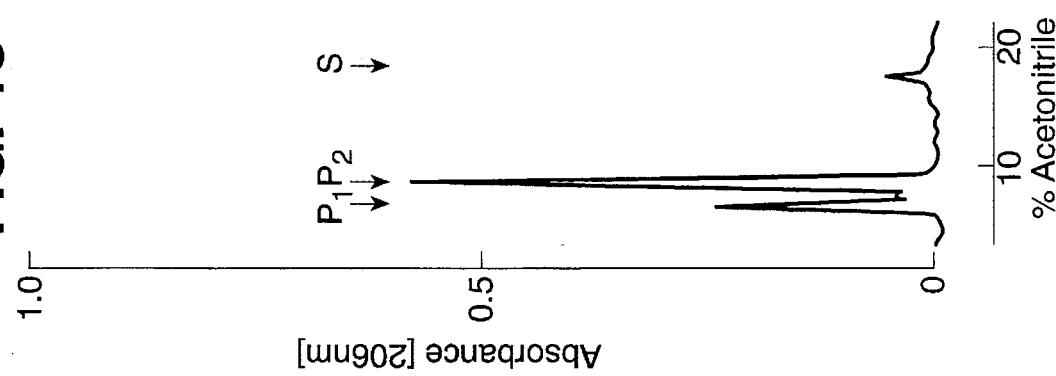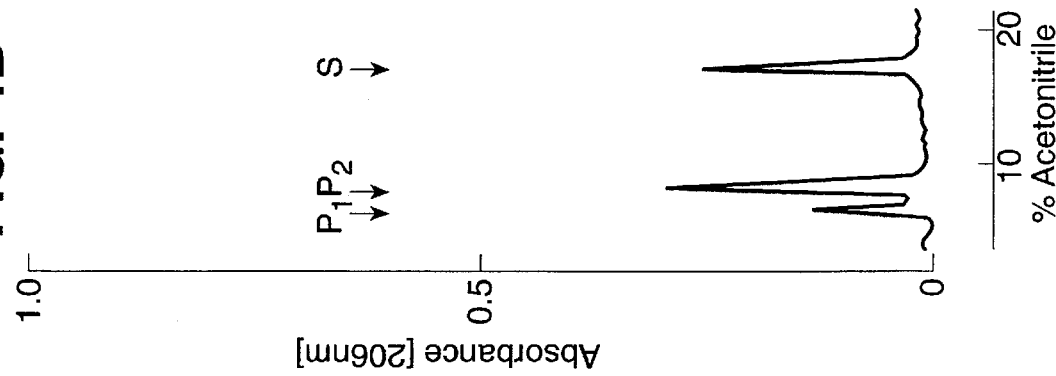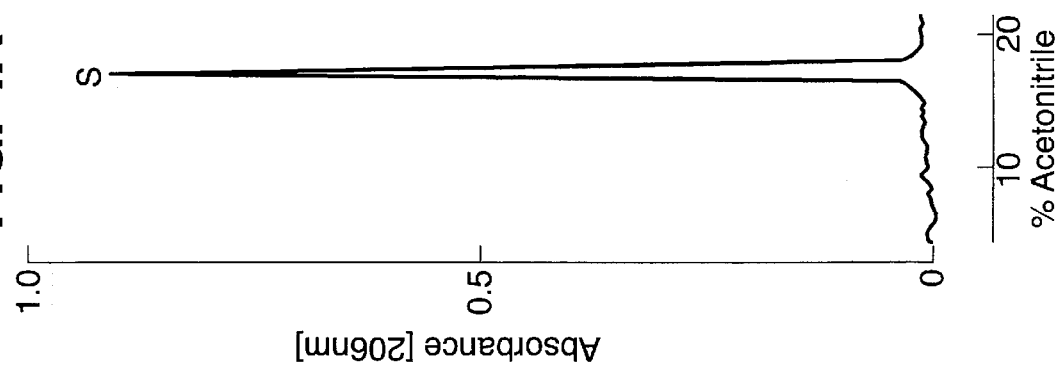

HIV PROTEASE GENE AND METHOD FOR ITS EXPRESSION

This is a continuation of Ser. No. 07/662,508 filed Feb. 28, 1991, now abandoned, which is a continuation of Ser. No. 07/218,304 filed Jul. 13, 1988, now abandoned, which is a continuation-in-part of U.S. Ser. No. 07/057,183 filed Jun. 1, 1987 which issued U.S. Pat. No. 5,252,477 on Oct. 12, 1993.

BACKGROUND OF THE INVENTION

1. Field of the Invention

This invention relates to synthetic genes and their expression products. Specifically, this invention relates to a synthetic protease gene and its expression product.

2. Description of the Related Art

The presence of protease protein in purified virion preparation was shown only by immunological techniques. The HIV protease sequence together with the gag and pol sequence of fusion proteins have been expressed from viral DNA in bacteria. Examples of each disclosures include: 1. Henderson, et al., 1988, "Human Retroviruses, Cancer and AIDS: Approaches to Prevention and Therapy", D. Bolognesi Ed. Published by Alan R. Liss Inc., New York, N.Y. pp. 135–147; 2. Dubouck, et al., 1987, [P.N.A.S., 84:8903–8906; and 3. Mous, et al., 1988, J. Virol, 62:1433–1436.

The primary sequences of the HIV protease has been determined by protein analysis and by the nucleotide sequence of the proviral DNA. It was thus determined that the protease is a 99 amino acid long protein encoded by a 297 bp long stretch of the HIV provirus. All previous experiments on the protease gene and on its expression were carried out by utilizing nucleotide sequences cloned out from the cDNA of the provirus. The inventors' work using synthetic DNA proves that the nucleotide sequence of the provirus DNA and also the deduced amino acid sequence are correct.

The complete nucleotide sequence of the HIV-1 proviral DNA was published by Ratner et al., 1985, Nature, 313:277–284. The sequence coding for the protease in the pol open reading frame of HIV was determined by previous analysis and corresponds to nucleotide 1833 to 2129. The N terminus and the C terminal amino-acids are proline and phenylalanine respectively. This sequence coding for the HIV-I 99 aminoacid protease is 297 bp long as follows.

The industry is lacking a synthetic DNA sequence that encodes a specific enzyme or protease which is essential for the completion replication of an infective human immunodeficiency virus (HIV). This DNA sequence is desirable to express this protease by recombinant methodology in bacteria and or in eukaryotic cells, and to produce enough protease for biochemical and physical characterization in order to design and produce potent inhibitors of this enzyme, and thereby to block the production of infective HIV particles.

BRIEF DESCRIPTION OF THE INVENTION

The invention is a gene for encoding a protease of human immunodeficiency virus. The gene consists essentially of a synthetic nucleotide sequence for a protease essential to infectivity of human immunodeficiency virus.

The protease is desirably a protease of HIV-1 or HIV-2 that is essential for the infectivity of these viruses.

The preferred embodiment of this inventions is a synthetic gene and the coding sequence for expression of the HIV-1 protease is represented above by the top rows of nucleotide sequence.

BRIEF DESCRIPTION OF THE DRAWING

FIG. 2 illustrates a strategy for the synthesis of the HIV-1 protease gene. The 3' overhangs are in lower case. The complementary strands (not shown) were provided with 3' overhangs to match the coding strands.

FIG. 3A through FIG. 3C illustrates the induction of the gene at various periods of time.

FIG. 4A through FIG. 4D illustrates the activity of the expressed protease using a synthetic peptide as a substrate.

DESCRIPTION OF THE PREFERRED EMBODIMENT

The invention is a synthetic DNA sequence for encoding a specific enzyme or protease. The protease is essential for the infectivity of the human immunodeficiency virus (HIV). The invented gene is desirable for the expression of the protease by recombinant methodology in bacteria and or in eukaryotic cells and the production of a commercially desirable amount of the protease for biochemical and physical characterization. This characterization is necessary for the design and production of potent inhibitors of this

```
   10         20         30         40         50         60
CCTCAGATCA CTCTTTGGCA ACGACCCCTC GTCACAATAA AGATAGGGGG GCAACTAAAG
GGAGTCTAGT GAGAAACCGT TGCTGGGGAG CAGTGTTATT TCTATCCCCC CGTTGATTTC 70         80         90        100        110        120
GAAGCTCTAT TAGATACAGG AGCAGATGAT ACAGTATTAG AAGAAATGAG TTTGCCAGGA
CTTCGAGATA ATCTATGTCC TCGTCTACTA TGTCATAATC TTCTTTACTC AAACGGTCCT 130        140        150        160        170        180
AGATGGAAAC CAAAAATGAT AGGGGGAATT GGAGGTTTTA TCAAAGTAAG ACAGTATGAT
TCTACCTTTG GTTTTTACTA TCCCCCTTAA CCTCCAAAAT AGTTTCATTC TGTCATACTA 190        200        210        220        230        240
CAGATACTCA TAGAAATCTG TGGACATAAA GCTATAGGTA CAGTATTAGT AGGACCTACA
GTCTATGAGT ATCTTTAGAC ACCTGTATTT CGATATCCAT GTCATAATCA TCCTGGATGT 250        260        270        280        290
CCTGTCAACA TAATTGGAAG AAATCTGTTG ACTCAGATTG GTTGCACTTT AAATTTT
GGACAGTTGT ATTAACCTTC TTTAGACAAC TGAGTCTAAC CAACGTGAAA TTTAAAA
``` enzyme. The invention also includes synthesis and expression of the protease gene of other retroviruses such as HIV-2, the human leukemia viruses such as HTLV I, II, and other human and animal RNA containing viruses causing leukemia sarcoma and other malignencies.

The nucleotide sequence for the preferred embodiment of this invention was obtained from a published paper by Ratner, et al., supra. The sequence in the pol open reading frame coding for the protease of HIV-1 corresponds to nucleotide 1833 to 2129. The N-terminal and the C-terminal amino-acids are proline and phenylalanine respectively. This sequence coding for the 99 aminoacid protease is 297 bp long as shown above. Minor substitutions of one or more bases in this and other genes useful in this invention can produce a variant gene capable of expressing the desired protease.

This sequence was synthesized as five fragments using the DNA synthesizer. Complementary strands corresponding to these five fragments were also synthesized. The 3' overhangs of four bases were provided for appropriate sequences to efficiently ligate each of the five fragments and to provide the correct coding sequence of the protease gene. Nucleotide ATG were added to the fragment corresponding to the 5' end of the gene and TAA at the 3' end.

Figure 1:
FIG. 1 presents the expressed HIV protease as analyzed in Western blot.
Figure 1:
Figure 1:

A procaryotic expression vector was used to clone and then to express the synthetic sequence coding for the protease. The expression can be in prokaryotes (bacteria) or in other appropriate expression systems. Recombinant clones screened by colony hybridization using a labelled fragment (62 bp) spanning the internal region of the protease gene. Positive clones were further analyzed for the size of the insert. Clones which answered positive were induced for expression and analyzed in Western blots to determine the protein product using specific antibodies. FIG. 1 gives an example. Of the clones screened so far, 3 clones have been identified to express a product of 11.5 kd, reacting against specific antibodies as illustrated in FIG. 1. Conditions for the induction of a protease gene were studied in $E.$ $coli$ and optimized. The inventors have shown that the gene product has specific protease activity, as it is capable of cleaving both synthetic and natural substrates. The enzyme has been purified by specific column chromatographic techniques, including affinity chromotography. The method of this invention can produce enough active protease to study the structure of the protease, its mechanisms of action, with a goal of devising specific inhibitors to this enzyme, of a therapeutic application for the treatment of the diseases, such as AIDS, caused by the viruses. Other embodiments of this invention can utilize a gene to express another protease such as the following gene for the HIV-2 protease.
CCTCAATTCTCTCTTTGGAAAAGACCAG-
TAGTCACAGCATACATTGAGGGTCAGCCA GTA-
GAAGTCTTGTTAGACACAGGGGCTGAC-
GACTCAATAGTAGCAGGAATAGAGTTA
GGGAACAATTATAGCCCAAAAATAG-
TAGGGGGAATAGGGGGATTCATAAATACCAAG
GAATATAAAAATGTAGAAATAGAAGT-
TCTAAATAAAAAGGTACGGGCCACCATAATG
ACAGGCGACACCCAATCAACATTTTTG-
GCAGAAATATTCTGACAGCCTTAGGCATGT CAT-
TAAATCTAC FIG. 1 demonstrates the expression of the HIV protease in $E.$ $coli$. Cells transformed with the synthetic sequence of HIV protease in an appropriate expression vector were induced and the bacterial lysate was electrophoresed in SDS-PAGE. After transfer of proteins into a nitrocellulose membrane, immunoblotting procedure was performed using the specific antibody to the HIV protease. Detection of Ag-Ab complex was made using $I^{125}$ protein A. The autoradiograph lane A represents $E.$ $coli$ transformed with the plasmid, and lanes B and C $E.$ $coli$ transformed with the plasmid bearing synthetic DNA encoding the HIV protease. On the left are protein molecular weight markers in kilodalton. The 11.5 kd band is the protease.

The synthetic DNA of the invention also obviates any need to manipulate (infectious) viral material and overcomes limitations in the quantities which can be obtained by other means.

EXAMPLES

The following materials and methods were used to perform the examples.
PLASMID, BACTERIAL STRAINS, AND CHEMICALS:

Plasmid PKK233-2, a procaryotic expression vector was purchased from Pharmacia. PKK233-2 was used to transform in a laq-q host, $E.$ $coli$ cell JM105 or RB791. The cells were selected in M9 minimal media containing 1 ug/ml thiamine, prior to using them for transformation. All chemicals utilized in the synthesis of oligonucleotides were from Applied Biosystems Inc. T4 polynucleotide kinase, DNA ligase, and Klenow fragment of $E.$ $coli$ DNA polymerase I were obtained from New England Biolabs. Restriction endonucleases, PMSF and IPTG were from Boehringer Mannheim, Bethesda Research Laboratories and Promega respectively.
DNA SYNTHESIS, PLASMID CONSTRUCTION AND SCREENING:

DNA fragments were synthesized using a ABI DNA synthesizer (model 381A). All synthetic fragments were purified by electrophoresis in a 12% polyacrylamide/8M urea sequencing gel. DNA was visualized by UV-shadowing and full-length fragments were eluted from the gel as known in the art. The full-length fragments were checked for their purity using standard techniques.

Appropriate complementary fragments were mixed in equimolar concentrations, annealed, kinased and ligated as described elsewhere. The efficiency of ligation was monitored by polyacrylamide gel electrophoresis. The linearized plasmid and the protease gene in appropriate concentrations were ligated and used for transformation of $E.$ $coli$, JM105. Recombinant clones were screened by colony hybridization using a 62 bp fragment labelled by kinasing. Small scale isolation of plasmid DNA from the recombinant clones was performed by the boiling method and the size of the inserts was visualized by autoradiography after labelling the 3' recessed terminal using the Klenow fragment of $E.$ $coli$ DNA polymerase.
ANTIBODIES TO THE HIV PROTEASE The polyclonal antibodies were raised in rabbits against (i) a complete synthetic sequence of 1 to 99 amino acids of the HIV-1 protease and (ii) a tridecapeptide corresponding to the C-terminus of the protease.
ANALYSIS OF THE EXPRESSED PROTEINS $E.$ $coli$ cells bearing the appropriate plasmid construct were grown to log phase, induced, and lysed by sonication. Total cell extracts were analysed by NaDodSO$_4$/PAGE and subjected to immunoblot analysis.
ASSAY FOR THE ACTIVITY OF THE EXPRESSED PROTEASE Oligopeptides were synthesized in a Peptide Synthesizer (Applied Biosystems Model 430A), according to the method previously published (Copeland and Oroszlan, 1981). The cleavage products were analysed by RP-HPLC on a uBondapak $C_{18}$ column (Waters Associates). Peak fractions were analysed for amino-acid composition using a Pico-Tag amino acid analyser (Waters Associates).

EXAMPLE 1

This example represents the preferred embodiment.
RESULTS:
SYNTHESIS OF THE FULL-LENGTH PROTEASE GENE:

The nucleotide sequence of the protease gene was taken from Ratner et al. The sequence in the pol open reading frame for the protease gene starts at nucleotide 1833 and ends at 2129, for coding 99 aminoacids. This sequence and its complement were synthesized as five individual fragments of approximately 60 bases as shown in FIG. 2. The 3' overhangs of 4 bases (shown in lower case) were provided for the fragments to selectively ligate the appropriate fragments to form the correct coding sequence. Translational initiation codon ATG and termination codon TAA were provided at the appropriate ends of the protease gene. A sequence was added to provide a protrusion at the 5' end of the gene, having a cohesive end compatible to the restriction enzyme site NcoI. The 5' protrustion at the 3' end of the gene was added to provide a Hind3 compatible end. The complementary strands (not shown) were provided with 3' overhangs to match the coding strands.

EXPRESSION OF THE SYNTHETIC HIV-1 PROTEASE GENE IN E. COLI

Three clones (PR-C, PR-H, and PR-J) bearing the correct coding sequence of 297 bp in the expression vector PKK233-2 were analyzed for expression to select conditions for the optimal induction of the gene. FIG. 3 shows examples of Western blot analysis of the gene product.

FIG. 3A through FIG. 3C illustrates expression of the synthetic protease gene in E. coli. Clone PR-C bearing the coding sequence to the protease was induced for expression. The proteins (75 ug of bacterial extract) were electrophoresed in a NaDodSO$_4$/PAGE transferred to nitrocellulose and subjected to immunoblot analysis using a mixture of the two protease specific rabbit polyclonal antibodies raised against (i) a complete synthetic sequence of 1–99 amino acids of the HIV-1 protease and (ii) a tridecapeptide corresponding to the C terminus of the protease. FIG. 3A shows the induction of the gene with 0.4 mM IPTG at various periods of time. FIG. 3B shows the induction for 30 minutes. With increasing concentrations of inducer IPTG. 1–5 represents mM concentration of IPTG at 0.28, 0.56, 1.12, 2.24, and 4.48, respectively. FIG. 3C showns the analysis after 60 minutes of induction with 1 mM IPTG and lysing the cells in various buffers. B1 denotes lysis of cells in 50 mM Tris-HCl at pH 7.0, 150 mM NaCl, 1 mM EDTA, 1 mM PMST, 1 mM DTT and 0.5 percent NP-40. B2 is the same as B1, but without NaCl and EDTA. B3 is in 50 mM potassium phosphate at pH 6.0, 1 mM PMSF and 1 mM DTT. B4 is the same as B3 with a pH of 6.5. G denotes control cells bearing just the plasmid PKK233-2 and induced. Three times more protein was loaded in this lane. Positions of protein molecular weight markers are inducated on the left in kilodaltons.

E. coli cells bearing plasmid PR-C were grown in Luria broth to an optical density of 0.4 A600 nm, and then induced at various periods of time for expression from the trc promotor by adding IPTG (isopropyl-beta-D-thiogalactopyranoside) at a concentration of 0.4 mM as seen in FIG. 3A. The cloned gene expressed a single, unfused protein band of 11.5 kd. Expression was maximal after 30 minutes of induction. This level decreased to about 25 percent at 60 minutes. There was no detectable expression after 120 minutes of induction and at 0 minutes. This pattern of induction was similar in the other clones (PR-H and PR-J) that were analyzed (not shown).

The results of the induction for 30 minutes with varying concentrations of inducer are shown in FIG. 3B. Induction with IPTG in the range of 1 mM to 4 mM resulted in maximum amount of expression. Similar data were obtained on clones PR-H and PR-J (not shown).

In order to select the conditions that efficiently solubilize the protease for enzymatic analysis, different buffer systems were used for the lysis of cells (clone PR-C) after optimal induction with 1 mM IPTG. It was observed that sonication in a buffer system of 50 mM Tris-cl at pH 7.5, 1 mM DTT, 1 mM PMSF and 0.5% nonidet P-40 released 50 to 70 percent of the protease in the soluble fraction (FIG. 3C). This was estimated by Western blot analysis aliquots of soluble extract and insoluble pellet for the content of the expressed product.

DEMONSTRATION OF SPECIFIC PROTEOLYTIC ACTIVITY

FIG. 4A through FIG. 4D illustrates the activity of the expressed protease using a synthetic peptide as a substrate. Protease assays were carried out with 22.5 ug of bacterial lysate at 37° C. obtained from clone PR-C, induced (FIG. 4A, FIG. 4B, FIG. 4C) uninduced (FIG. D), and control cells bearing just the plasmid PKK233-2 (data not shown). THe nonapeptide was used as a substrate in reaction buffer (0.25M potassium phosphate), pH 7.0, 0.5 percent (v/v) NP 40, 5 percent (v/v) glycerol, 5 mM Dithiotreit and 2 M NACl. Aliquots of 25 ul each were taken at 0 hours (A), 1 hour (B) 3 hours (C) and 6 hours (D) analyzed by RP-HPLC. S denotes the substrate and P1 and P2, cleavage products 1 and 2 respectively.

To assess the activity of the cloned HIV-1 Protease a synthetic nonapeptide corresponding to the HIV-1 p17–p24 cleavage site (Henderson, et al. 1988) was used as a substrate (4E). The substrate in reaction buffer was mixed with aliquots of various cell extracts (see description of FIG. 4A through FIG. 4D above) and incubated at 37° C. Equal eliquots of incubation mixture were taken at various time points and analyzed by RP-HPLC. The substrate in the 0 hour sample eluted as a single peak as shown in FIG. 4A. After incubation for 1 hour, two newly appearing peaks, products labelled P1 and P2, can be seen, correlating with a signifant decrease of the substrate peak. Subsequent amino acid analysis of the recovered peaks demonstrated that product 1 and product 2 corresponded to the expected cleavage products as shown in Table 1 proving a Tyr-Pro bond cleavage, which is the determined natural cleavage site. Extended incubation for 3 hours showed a further decrease of the substrate peak and substantial increase in the peak height of product 1, indicating progression of the hydrolysis of the Tyr-Pro bond. However, the peak of product 1 seems to be smaller as expected since the absorbance of the tetrapeptide Pro-Ile-Val-Glu-NH$_2$ is substantially smaller than that of the pentapeptide having a free COOH-terminal tyrosine. An increase of product 1 and 2 after 3 hours of incubation showed a corresponding decrease of the substrate peak.

No cleavage products have been detected in reactions using extracts from uninduced cells, clone PR-C (FIG. 4D) and of control cells (control plasmid PKK233-2; data not shown). There was no decrease in the substrate peak even after 6 hours of incubation (FIG. 4D) indicating that the nonapeptide is resistent to degradation by bacterial proteases. This makes this substrate especially useful for assaying viral protease activities in crude extracts, facilitating purification and isolation of the protease.

The amino acid composition data for the substrate and its cleavage products are shown in Table 1. The amounts of observed amino acids correspond clearly to the expected amounts demonstrating that the cleavage occurs at the expected cleavage site of the synthetic peptide corresponding to the p17–p24 site of the gag precursor.

Table 1

| | Amino acid composition of the substrate and the cleavage products | | | | | |
|---|---|---|---|---|---|---|
| | Substrate | | product 1 | | product 2 | |
| Amino acids | Predicted | Recovered | Predicted | Recovered | Predicted | Recovered |
| Asp | 1 | 1.06 | 0 | 0.01 | 1 | 0.94 |
| Glu | 2 | 2.06 | 1 | 1.00 | 1 | 1.00 |
| Ser | 1 | 0.98 | 0 | 0.01 | 1 | 0.89 |
| Pro | 1 | 1.05 | 1 | 0.19 | 0 | 0.03 |
| Tyr | 1 | 1.06 | 0 | 0.01 | 1 | 1.01 |
| Val | 2 | 1.87 | 1 | 0.43* | 1 | 1.16 |
| Ile | 1 | 0.92 | 1 | 0.45* | 0 | 0.02 |

*The observed amounts of Val and Ile were found lower than expected in product 1 due to a frequently observed inefficient hydrolysis of the Ile—Val bond.

We claim:

1. A construct comprising:

(i) a DNA gene sequence from an HIV-1 species consisting of:

```
         10         20         30
    CCTCAGATCA CTCTTTGGCA ACGACCCCTC 40         50         60
    GTCACAATAA AGATAGGGGG GCAACTAAAC 70         80         90
    GAAGCTCTAT TAGATACAGG AGCAGATGAT 100        110        120
    ACAGTATTAG AAGAAATGAG TTTGCCAGGA 130        140        150
    AGATGGAAAC CAAAAATGAT AGGGGGAATT 160        170        180
    GGAGGTTTTA TCAAAGTAAG ACAGTATGAT 190        200        210
    CAGATACTCA TAGAAATCTG TGGACATAAA 220        230        240
    GCTATAGGTA CAGTATTAGT AGGACCTACA 250        260        270
    CCTGTCAACA TAATTGGAAG AAATCTGTTG 280        290
    ACTCAGATTG GTTGCACTTT AAATTTT
``` or allelic or species variations thereof, said variations encoding the same amino acid sequence as encoded by said DNA gene sequence, and (ii) an expression vector wherein said construct is capable of expressing in host cells a single unfused recombinant protein encoded by said DNA gene sequence or said variations thereof, wherein said recombinant protein has proteolytic activity.

2. A construct according to claim 1, wherein the host cell is *E. coli*.

3. A construct comprising:

(i) a DNA gene sequence consisting of:

```
        10         20         30         40         50
CCTCAGATCA CTCTTTGGCA ACGACCCCTC GTCACAATAA AGATAGGGGG 60         70         80         90        100
GCAACTAAAC GAAGCTCTAT TAGATACAGG AGCAGATGAT ACAGTATTAG 110        120        130        140        150
AAGAAATGAG TTTGCCAGGA AGATGGAAAC CAAAAATGAT AGGGGGAATT 160        170        180        190        200
GGAGGTTTTA TCAAAGTAAG ACAGTATGAT CAGATACTCA TAGAAATCTG 210        220        230        240        250
TGGACATAAA GCTATAGGTA CAGTATTAGT AGGACCTACA CCTGTCAACA 260        270        280        290
TAATTGGAAG AAATCTGTTG ACTCAGATTG GTTGCACTTT AAATTTT,
``` and (ii) an expression vector wherein said construct is capable of expressing in *E. coli* a recombinant protein encoded by said DNA gene sequence, wherein said recombinant protein has proteolytic activity.

4. A method of producing an isolated recombinant protein consisting essentially of the steps of:

(i) introducing into host cells the DNA gene sequence from an HIV-1 species consisting of:

```
         10         20         30
CCTCAGATCA CTCTTTGGCA ACGACCCCTC 40         50         60
GTCACAATAA AGATAGGGGG GCAACTAAAC 70         80         90
GAAGCTCTAT TAGATACAGG AGCAGATGAT 100        110        120
ACAGTATTAG AAGAAATGAG TTTGCCAGGA 130        140        150
AGATGGAAAC CAAAAATGAT AGGGGGAATT 160        170        180
GGAGGTTTTA TCAAAGTAAG ACAGTATGAT 190        200        210
CAGATACTCA TAGAAATCTG TGGACATAAA 220        230        240
GCTATAGGTA CAGTATTAGT AGGACCTACA 250        260        270
CCTGTCAACA TAATTGGAAG AAATCTGTTG 280        290
ACTCAGATTG GTTGCACTTT AAATTTT
``` or allelic or species variations thereof, said variations encoding the same amino acid sequence as encoded by said DNA gene sequence, said DNA gene sequence operably linked to a promoter, (ii) culturing said host cells under conditions such that said sequence or allelic or species variation thereof is expressed and said protein thereby produced, and (iii) isolating said protein.

5. A method of claim 4 wherein the protein is purified by affinity chromatography.

6. A method according to claim 4 wherein the recombinant protein has proteolytic activity.

7. A method according to claim 4 wherein the host cell is *E. coli*.

8. A method of producing an isolated recombinant protein consisting essentially of the steps of:

(i) introducing into *E. coli* the DNA gene sequence consisting of:

```
         10         20         30
CCTCAGATCA CTCTTTGGCA ACGACCCCTC 40         50         60
GTCACAATAA AGATAGGGGG GCAACTAAAC 70         80         90
GAAGCTCTAT TAGATACAGG AGCAGATGAT 100        110        120
ACAGTATTAG AAGAAATGAG TTTGCCAGGA 130        140        150
AGATGGAAAC CAAAAATGAT AGGGGGAATT 160        170        180
GGAGGTTTTA TCAAAGTAAG ACAGTATGAT 190        200        210
CAGATACTCA TAGAAATCTG TGGACATAAA 220        230        240
GCTATAGGTA CAGTATTAGT AGGACCTACA 250        260        270
CCTGTCAACA TAATTGGAAG AAATCTGTTG 280        290
ACTCAGATTG GTTGCACTTT AAATTTT
``` said DNA gene sequence operably linked to a promoter, (ii) culturing said *E. coli* under conditions such that said sequence is expressed and said protein thereby produced, and (iii) isolating said protein.

9. A method according to claim 8 wherein the recombinant protein has proteolytic activity.

* * * * *